United States Patent [19]

Guzik

[11] 4,197,259

[45] Apr. 8, 1980

[54] PREPARATION OF HALOANILINE

[75] Inventor: Frederick F. Guzik, Wadsworth, Ohio

[73] Assignee: PPG Industries, Inc., Pittsburgh, Pa.

[21] Appl. No.: 14,172

[22] Filed: Feb. 22, 1979

[51] Int. Cl.$^2$ ............... C07C 85/00; C07C 85/04
[52] U.S. Cl. .................................. 260/581; 260/575
[58] Field of Search .................................. 260/581

[56] References Cited
FOREIGN PATENT DOCUMENTS 2734368  9/1978  Fed. Rep. of Germany ........... 260/581

OTHER PUBLICATIONS

Wotiz et al, "J. Org. Chem.", vol. 24, pp. 595-598 (1959).
Gilman et al, "J.A.C.S.", vol. 74, pp. 3027-3029 (1952).
Sidgwick, "Organic Chemistry of Nitrogen", p. 143 (1966).
Patai, "The Chemistry of the Amino Group", pp. 58-60 (1968).

*Primary Examiner*—John Doll
*Attorney, Agent, or Firm*—Edward J. Whitfield

[57] ABSTRACT

Haloaniline is produced in high yield by reacting halobenzene with a mixture containing a metal amide and a controlled molar excess of liquid ammonia based on the moles of halobenzene.

4 Claims, No Drawings

PREPARATION OF HALOANILINE

BACKGROUND OF THE INVENTION

Chloroaniline, e.g., m-chloroaniline, is typically prepared by chlorinating nitrobenzene and reducing the resulting m-chloronitrobenzene product. The intermediate compounds formed in this process are chemically related to known explosive materials, particularly 2-chloro-4-nitrotoluene, and production of m-chloroaniline by this route poses potential hazards.

Since it is known to prepare haloaniline by reacting alkali metal amide with halobenzene in liquid ammonia, as described, for example, in an article entitled "Low Temperature Amination of Aromatic Polyhalides", Wotiz et al., *Journal Organic Chemistry*, Vol. 24, pp. 595-598 (1959), it was thought that this procedure might be a more viable route to m-chloroaniline production. Although the process described by Wotiz et al enables the production of m-chloroaniline by low temperature amination of o-dichlorobenzene, the yield of m-chloroaniline is disappointingly low with inordinately long reaction times. In addition, objectionable quantities of undesirable o-chloroaniline and p-chloroaniline isomers are also produced. For example, Wotiz et al reports an m-chloroaniline yield of only 26 percent after 16 hours reaction time, when preparing m-chloroaniline by reacting sodium amide with o-dichlorobenzene in liquid ammonia.

An improved process has been found which enables the production of haloaniline, e.g., m-chloroaniline, in high yield and in shorter reaction times than heretofore believed possible.

SUMMARY OF THE INVENTION

Haloaniline, e.g., m-chloroaniline, is produced in high yield by reacting halobenzene, e.g., o-dichlorobenzene, with a mixture containing a metal amide, e.g., sodium amide, and a controlled molar excess of liquid ammonia based on the moles of halobenzene starting material.

DESCRIPTION OF THE INVENTION

In accordance with this invention, it has been found that in the preparation of m-chloroaniline by the low temperature amination of o-dichlorobenzene the yield of m-chloroaniline is dependent on the molar ratio of ammonia to o-dichlorobenzene. Although the process of the invention has been found to be particularly applicable to the preparation of m-chloroaniline by low temperature amination of o-dichlorobenzene and is described with particular reference thereto, it is contemplated that the process of this invention, in its broadest aspects, would be equally applicable to the preparation of other haloanilines of the type described, for example, in the above cited Wotiz et al article, wherein the amination of halobenzene in liquid ammonia proceeds by way of an elimination-addition mechanism via the formation of a benzyne intermediate.

For example, the reaction mechanism involved in the present invention may be represented as follows, wherein o-dichlorobenzene and sodium amide are used as starting materials:

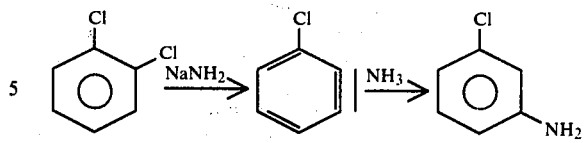

The metal amide-liquid ammonia mixture contains sufficient metal amide to provide at least a 2:1 molar ratio of metal amide to halobenzene and sufficient ammonia to provide at least a 50:1 molar ratio of ammonia to halobenzene. Although there is no particular upper limit to the amount of metal amide, it has been observed that at molar ratios of metal amide to halobenzene in excess of about 4:1, there is no significant increase either in the extent of conversion of halobenzene or in the yield of haloaniline.

However, with regard to the ammonia, it has been found that at mole ratios of ammonia to halobenzene in excess of about 80:1, the yield of haloaniline decreases significantly. It has been observed that optimum yield, i.e., greater than about 70 percent, of haloaniline is obtained at a molar ratio of ammonia to halobenzene of between about 65:1 to 75:1.

Consequently, in order to obtain acceptable yields of haloaniline, i.e., at least about 60 percent, preferably in excess of 70 percent, the metal amide-liquid ammonia mixture contains sufficient metal amide to provide from about 2 to 4 moles of metal amide and from about 50 to 80 moles, preferably 65 to 75 moles, of ammonia per mole of halobenzene starting material.

The reaction between the metal amide-liquid ammonia mixture and the halobenzene is conducted under substantially anhydrous conditions and typically at atmospheric pressure and at a temperature near the boiling point of liquid ammonia, i.e., $-33.74°$ C., preferably from about $-30°$ C. to about $-35°$ C. Although the reaction may be conducted at a temperature significantly higher than the boiling point of liquid ammonia, sufficient pressure would be required to maintain the ammonia in the liquid phase.

As beforesaid, although the invention is particularly applicable to producing m-chloroaniline by the amination of o-dichlorobenzene, it is contemplated that the invention is equally applicable to the production of a variety of haloanilines by the amination of the corresponding halobenzenes. Some examples of other halobenzenes that are contemplated for use as starting materials according to the process of the invention are 1,2,4-trichloro-benzene, 1,2-dichloro-4-bromo-benzene, 1,2-dibromo-benzene, 1,3,5-trichloro-benzene, 1,3,5-tribromo-benzene, 1-methoxy-2-chloro-benzene, 1-methoxy-2-bromo-benzene, 1-trifluoromethyl-2-chloro-benzene, 1-trifluoromethyl-2-bromo-benzene and the like.

The metal amides suitable for use in the invention include alkali metal amides, e.g., sodium amide, potassium amide, lithium amide and the like. Alkaline earth metal amides, such as barium amide and calcium amide may also be used. Sodium amide is preferred.

In order to produce as high a purity product as possible, the metal amide and halobenzene starting materials should, of course, be as pure as possible. Halobenzene, e.g., o-dichlorobenzene, having an assay of at least about 99 percent and metal amide, e.g., sodium amide, having an assay of at least about 90 percent, are preferred for use in accordance with the invention.

The reaction between halobenzene and the metal amide-ammonia mixture proceeds at a very rapid rate and appears to proceed as rapidly as the halobenzene is added. The reaction, however, is highly exothermic and consequently the rate of halobenzene addition to the metal amide ammonia mixture would be governed by the heat removal capacity of the system. In a typical practice of the invention, halobenzene is added to a continuously stirred mixture of metal amide and ammonia, the rate of addition of halobenzene, being regulated so that the temperature is maintained in the range of −30° C. to −35° C. At the completion of halobenzene addition, the reaction mixture is typically quenched by the rapid addition of, for example, a lower aliphatic alcohol, e.g., methanol, ethanol, propanol or the like, to liberate the free haloaniline. Excess ammonia is removed by, for example, evaporation, the reaction mixture is brought up to ambient temperature, and the haloaniline is separated therefrom by conventional means, such as, for example, by extraction with an organic solvent, e.g., methylene chloride.

According to the preferred practice of this invention, m-chloroaniline assaying in excess of 98 percent, in yields in excess of 70 percent, with substantially quantitative conversion of o-dichlorobenzene may be routinely obtained.

The invention is further illustrated by the following example, which demonstrates the effect of the ammonia to halobenzene molar ratio on the yield of haloaniline.

EXAMPLE

A. Starting Materials

1. The sodium amide used was obtained from Fike Chemicals, Inc. (Lot H-725) and assayed at 90.2 percent.

2. The ammonia was anhydrous grade obtained from Union Carbide Corp.

3. The o-dichlorobenzene was obtained from Eastman Chemicals Co. (Lot B6G) and assayed 99.4 percent ortho, 0.60 percent meta and 0.49 percent para.

B. Experimental Procedure

A three-neck flask, a clean beaker, powder funnel and scoop-type spatula were dried overnight in an oven at about 90° C. and transferred hot to a prepurified nitrogen-filled glove bag. When this equipment had cooled, the glove bag was evacuated and re-pressurized with nitrogen. Sodium amide was kept in the nitrogen-filled glove bag between experiments. 21 grams (0.48 mole, 90.2% assay basis) sodium amide were weighed into the beaker and charged to the flask using the powder funnel to avoid spillage. The flask was stoppered using a hose-connecting adapter with stopcock in one neck, removed from the glove bag and a nitrogen line attached. A Teflon paddle on a glass stirring rod through a Trubore bearing and an offset adapter, both oven dried, were installed on the reaction flask with a stream of nitrogen padding the sodium amide. One neck of the adapter was connected to the ammonia cylinder and the other neck fitted with a dry ice/acetone filled cold finger condenser vented to the atmosphere through a Drierite drying tube. Sufficient ammonia was condensed into the flask containing the sodium amide to provide the desired molar ratio of ammonia to o-dichlorobenzene. After addition of the ammonia, the adapter connection to the nitrogen supply was replaced by a dropping funnel with an equalizing side arm containing 32.6 grams (0.22 mole) of o-dichlorobenzene. The o-dichlorobenzene was added to the well-stirred slurry of sodium amide and liquid ammonia over a period of about 6 to 8 minutes. During the addition of o-dichlorobenzene, vigorous boiling of the reaction mixture and a steady reflux of liquid from the condenser were apparent. During o-dichlorobenzene addition, the reaction mixture was maintained at a temperature of between −32° C. to −33° C. After completion of the addition of o-dichlorobenzene, the reaction mixture was stirred with ammonia reflux for an additional 6 to 8 minutes. Fifty milliliters of methanol were then rapidly added to the flask, and the condenser was replaced with a Vigreux column and excess ammonia was evaporated, while the flask was warmed with a water bath until the reaction mixture was at ambient temperature. After the reaction mixture reached ambient temperature, 150 milliliters of methylene chloride and 75 milliliters of distilled water were added to the flask, the mixture was thoroughly stirred and transferred to a separatory funnel. The reaction flask was rinsed once with a mixture of 150 milliliters of methylene chloride and 75 milliliters water, and the rinse was added to the separatory funnel. No visible residues were left in the flask after rinsing. The mixture in the separatory funnel was permitted to phase separate, and the organic layer was extracted once with 200 milliliters and three times with 100 milliliters of aqueous 1 Normal hydrochloric acid. The mixture was again permitted to phase separate, and the organic layer was removed and dried with 10 grams of anhydrous magnesium sulfate, filtered, and concentrated on a rotary evaporator at reduced pressure, i.e., about 30 millimeters of mercury at 25°-30° C. The residue was designated as the acid insoluble fraction containing unreacted o-dichlorobenzene and soluble tarry non-basic by-products. The amount of unreacted o-dichlorobenzene in the acid insoluble fraction was determined by gas chromatography. The combined aqueous acid extracts were adjusted to a pH of about 13, with aqueous 10 percent sodium hydroxide solution and extracted with three 100 milliliter portions of methylene chloride. The combined methylene chloride extracts were dried with 10 grams anhydrous magnesium sulfate, filtered, and concentrated on a rotary evaporator at reduced pressure, i.e., about 30 millimeters mercury at 25°-30° C. This residue, designated as the acid soluble fraction, constituted the yield of crude m-chloroaniline. Analysis of this fraction for isomer distribution was made by high performance liquid chromatography.

The foregoing procedure was followed, using various molar ratios of ammonia to o-dichlorobenzene, namely, 18:1, 32:1, 52:1, 72:1 and 100:1. The results of these experimental Runs 1 to 5 are summarized on Table 1.

As can be seen from an inspection of the data in Table 1, the yield of m-chloroaniline increases as the ammonia to o-dichlorobenzene molar ratio increases. From a plot of the ammonia o-dichlorobenzene molar ratio versus yield of m-chloroaniline, it is determined that the optimum yield of m-chloroaniline appears to be obtained at a molar ratio of ammonia to o-dichlorobenzene of between 65 to 75:1. At molar ratios of ammonia to o-dichlorobenzene much in excess of 80:1, the yield of m-chloroaniline significantly decreases.

Although the invention has been described in the foregoing by reference to specific details and embodiments thereof, it is not intended that the invention be so limited to such specific details and embodiments except to the extent that the same appear in the appended claims.

Table 1

| Run No. | 1 | 2 | 3 | 4 | 5 |
|---|---|---|---|---|---|
| Molar Ratio $NH_3$:-o-DCB | 18:1 | 32:1 | 52:1 | 72:1 | 100:1 |
| Percent Conversion of o-DCB | 95 | 100 | 98 | >99 | 94 |
| Percent Yield of MCA | 43 | 59 | 64 | 78 | 58 |
| Isomer Distribution: | | | | | |
| % MCA | 95.1 | 95.0 | 98.6 | 98.7 | 98.7 |
| % OCA | 0.9 | 1.2 | 1.1 | 0.8 | 0.9 |
| % PCA | 0.3 | 0.3 | 0.3 | 0.4 | 0.5 |
| % Other | 3.4 | 3.2 | — | — | — | o-DCB = ortho-Dichlorobenzene
$NH_3$ = Ammonia
MCA = meta-Chloroaniline
OCA = ortho-Chloroaniline
PCA = para Chloroaniline

I claim:

1. In a process for the preparation of haloaniline by the amination of halobenzene wherein alkali metal amide is reacted with halobenzene in liquid ammonia and wherein haloaniline is recovered from the reaction mixture the improvement comprising adding halobenzene to a mixture containing metal amide and liquid ammonia said mixture containing at least about 2 moles of metal amide per mole of halobenzene added and from about 50 to about 80 moles of liquid ammonia per mole of halobenzene added.

2. The process of claim 1 wherein the halobenzene is o-dichlorobenzene.

3. The process of claim 1 wherein the metal amide is sodium amide.

4. The process of claim 1 wherein the metal amide liquid ammonia mixture contains from about 65 to 75 moles of liquid ammonia per mole of halobenzene added.

* * * * *